United States Patent [19]
Rabinovitz et al.

[11] Patent Number: 5,385,933
[45] Date of Patent: Jan. 31, 1995

[54] METHOD FOR THE TREATMENT OF CANCER BY USE OF THE COPPER COMPLEX OF S-(METHYLTHIO)-DL-HOMOCYSTEINE OR THE L-ENANTIOMORPH THEREOF

[75] Inventors: Marco Rabinovitz; Joyce M. Fisher, both of Bethesda, Md.

[73] Assignee: The United States of America as represented by the Department of Health and Human Services, Washington, D.C.

[21] Appl. No.: 901,261

[22] Filed: Jun. 19, 1992

Related U.S. Application Data

[63] Continuation-in-part of Ser. No. 315,911, Feb. 27, 1989, Pat. No. 5,124,351.

[51] Int. Cl.$^6$ .................. A61K 31/30; A61K 31/195
[52] U.S. Cl. .................................. 514/499; 514/500; 514/562
[58] Field of Search .................. 514/499, 500, 562

[56] References Cited

U.S. PATENT DOCUMENTS 5,124,351  6/1992  Rabinovitz et al. ............... 514/499

OTHER PUBLICATIONS

Christopherson et al., "Potent Inhibitors of De Novo Pyrimidine and Purine Biosynthesis as Chemotherapeutic Agents," *Medicinal Research Reviews,* 10 (4): 505–548. 1990.
Livingston et al., "Glutamine Antagonists in Chemotherapy," *Adv. Pharmacol. Chemotherap.,* 8: 57–120. 1970.
Mohindru et al., "2,9–Dimethyl–1, 10–Phenanthroline (Neocuproine): A Potent, Copper-Dependent Cytotoxin With Anti-Tumor Activity," *Biochemical Pharmacology,* 32 (23): 3627–3632. 1983.
Neil et al., "Studies of the Biochemical Pharmacology of the Fermentation–Derived Antitumor Agent, (αS, 5S)-α-Amino-3-Chloro-4, 5-Dihydro-5-Isoxazoleacetic Acid (AT–125)," *Adv. Enzyme Regul.,* 17: 375–398. 1978.
Rabinovitz et al., "Evidence for a Copper:S–(Methylthio)–L–homocysteine Complex as a Glutamine Antagonist of Cytidine Triphosphate Synthesis in L1210 Murine Leukemia Cells," *Molecular Pharmacology,* 34: 401–406. 1988.
Starkebaum et al., "Endothelial Cell Injury Due to Copper-catalyzed Hydrogen Peroxide Generation from Homocysteine," *The Journal of Clinical Investigation, Inc.,* 77: 1370–1376. 1986.

*Primary Examiner*—Raymond J. Henley, III
*Assistant Examiner*—T. J. Criares
*Attorney, Agent, or Firm*—Leydig, Voit & Mayer, Ltd.

[57] ABSTRACT

A composition and a method for inhibiting cellular proliferation, such as the abnormal cellular proliferation characteristic of cancer cells. The method comprises the administration to a mammal, in particular a human, of an effective amount of S-(methylthio)-DL-homocysteine or S-(methylthio)-L-homocysteine, either simultaneously or sequentially, with an effective amount of a copper chelate such that an effective amount of an inhibitory complex forms in the mammal between the S-(methylthio)-homocysteine and the copper of the cooper chelate. The inhibitory complex is capable of inhibiting the proliferation of cells contacted by the inhibitory complex.

28 Claims, 9 Drawing Sheets

METHOD FOR THE TREATMENT OF CANCER BY USE OF THE COPPER COMPLEX OF S-(METHYLTHIO)-DL-HOMOCYSTEINE OR THE L-ENANTIOMORPH THEREOF

This patent application is a continuation-in-part of co-pending U.S. patent application Ser. No. 07/315,911, filed Feb. 27, 1989 and issued as U.S. Pat. No. 5,124,351.

FIELD OF THE INVENTION

The present invention pertains to the inhibition of cellular proliferation, such as the abnormal cellular proliferation associated with cancer cells, by the co-administration of S-(methylthio)-DL-homocysteine or S-(methylthio)-L-homocysteine and a copper chelate.

BACKGROUND OF THE INVENTION

S-(methylthio)-homocysteine (SMETH) was disclosed in Japanese Patent Publication Kokai No. 77-83710. dated Jul. 12, 1977 (C.A. 88:23393m). The patent publication, however, did not recognize the potential of SMETH as an effective therapeutic agent, particularly the potential of SMETH to function as a potent glutamine antagonist in cancer cells.

Natural antibiotics, such as 6-diazo-5-oxo-norleucine, azaserine and acivicin, are glutamine antagonists that are effective anti-cancer agents. However, these antibiotics suffer from the disadvantage of low biochemical specificity. Accordingly, there remains a need for an effective therapeutic agent with high biochemical specificity, which inhibits cellular proliferation, such as the abnormal cellular proliferation associated with cancer cells. In particular, a potent glutamine antagonist, which overcomes the disadvantage of low biochemical specificity of natural antibiotic glutamine antagonists, is desirable.

The present invention overcomes the deficiencies in the prior art by providing a potent glutamine antagonist, which forms through the combination of SMETH and the copper of a copper chelate, that inhibits cellular proliferation, such as the abnormal cellular proliferation associated with cancer cells, with a high degree of biochemical specificity. Also provided are compositions, methods of treatment, and pharmaceutical kits.

SUMMARY OF THE INVENTION

The present invention provides a method of inhibiting cellular proliferation, such as the abnormal cellular proliferation characteristic of cancer cells, in a mammal, in particular a human, which method comprises the administration of an effective amount of DL or L SMETH and an effective amount of a copper chelate such that an effective amount of an inhibitory complex forms in the mammal between the SMETH and copper of the copper chelate so as to inhibit the proliferation of cells contacted by the inhibitory complex.

The method of the present invention may additionally comprise the administration of an effective amount of one or more glutamine aminotransferase inhibitors.

Additionally, or alternatively, the method of the present invention may comprise the administration of an effective amount of one or more amino acids that potentiate the activity of SMETH (DL or L).

Depending on the particular application at hand, the action of the SMETH-copper complex may be prevented or reversed by the subsequent administration of a compound, such as glutamine or cytidine.

The present invention also provides a pharmaceutical composition comprising an effective amount of SMETH (DL or L), an effective amount of a copper chelate, and a pharmaceutically acceptable carrier.

The present invention also provides pharmaceutical kits, which separately comprise an effective amount of SMETH (DL or L) and an effective amount of a copper chelate, which upon combination form an effective amount of an inhibitory complex that is capable of inhibiting the proliferation of cells contacted by the inhibitory complex.

It is an object of the present invention to provide a composition and a method for inhibiting cellular proliferation in a mammal, in particular a human.

In particular, it is an object of the present invention to provide a composition and a method for inhibiting abnormal cellular proliferation such as that which is characteristic of cancer cells.

It is another object of the present invention to provide a nontoxic composition and method for inhibiting cellular proliferation in mammals, in particular humans.

It is still another object of the present invention to provide a composition and a method for treating cancer in mammals, in particular humans.

It is yet another object of the present invention to provide a composition and a method, both of which are characterized by a high degree of biochemical specificity, for treating cancer in mammals, in particular humans.

These and other objects and advantages of this invention, as well as additional inventive features, will become apparent from the detailed description set forth herein.

DESCRIPTION OF THE PREFERRED EMBODIMENTS

Figure 1:
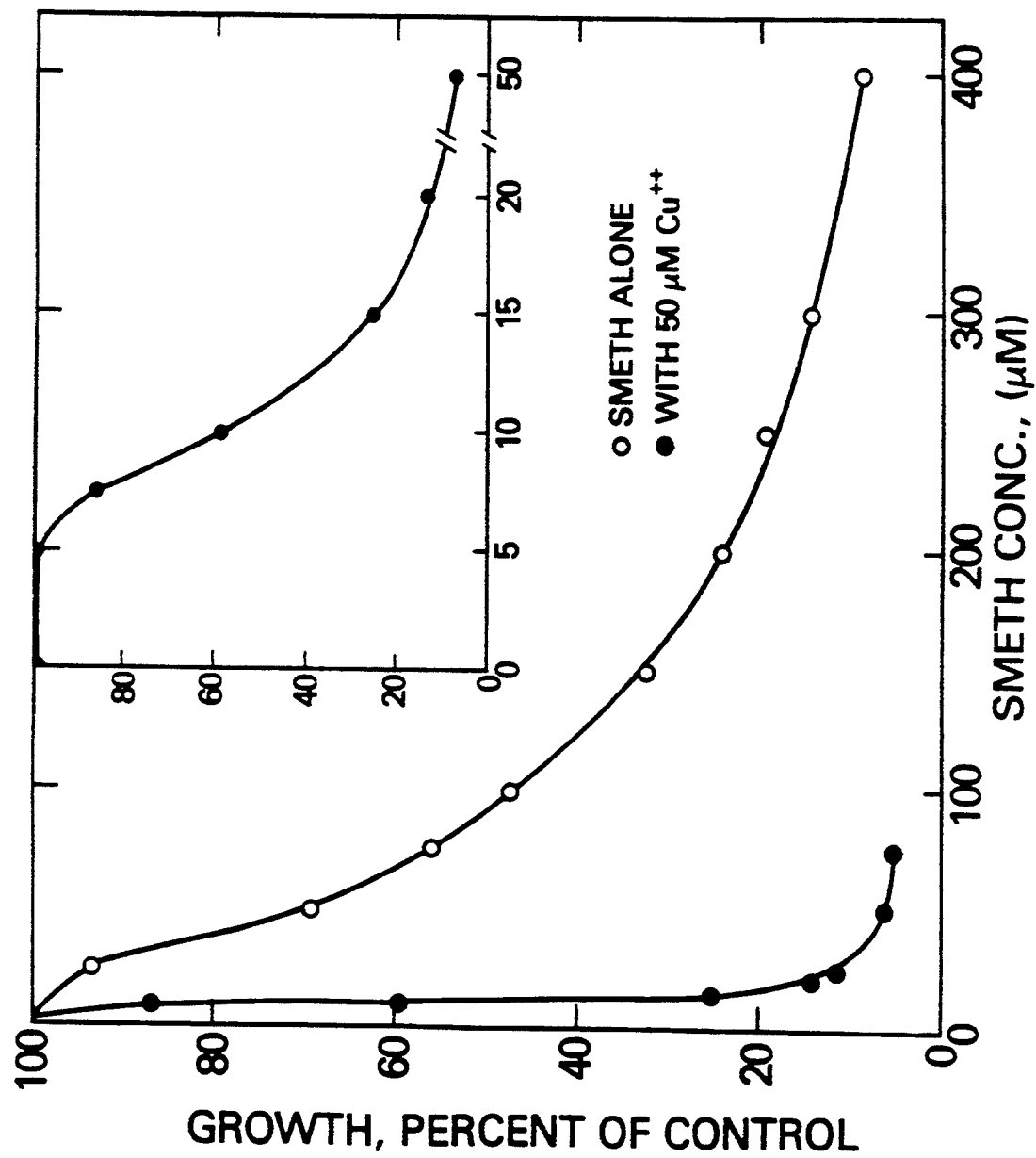
FIG. 1 shows the inhibition of growth of L1210 cells in culture by S-(methylthio)-DL-homocysteine (DL-SMETH) and its potentiation by copper.

The present invention provides a method of inhibiting cellular proliferation, such as the abnormal cellular proliferation that is characteristic of cancer cells, in a mammal, in particular a human. The method comprises administering to a mammal an effective amount of S-(methylthio)-homocysteine selected from the group consisting of the L stereoisomer and a racemic mixture of the D and L stereoisomers of S-(methylthio)-homocysteine (SMETH (L or DL)) and an effective amount of a copper chelate such that an effective amount of an inhibitory complex forms in the mammal between the SMETH and the copper of the copper chelate so as to inhibit the proliferation of cells contacted by said effective amount of said inhibitory complex.

The SMETH and the copper chelate may be administered by any suitable method. One skilled in the art will appreciate that many suitable methods of administering SMETH and a copper chelate to an animal in the context of the present invention, in particular a human, are available, and, although more than one route can be used to administer a particular compound, a particular route can provide a more immediate and more effective reaction than another route. Preferably, the SMETH and the copper chelate are administered by injection or infusion, either intravenously or intraperitoneally.

The SMETH may be either a racemic mixture of the D and L stereoisomers (DL-SMETH) or the L stereoisomer alone (L-SMETH). The copper chelate may be any suitable copper chelate. The copper chelate is preferably non-toxic, and the copper of the copper chelate preferably readily forms a complex with SMETH that inhibits cellular proliferation. Preferably, the copper chelate is a chelate of any bis-(thiosemicarbazone), such as 2-keto-3-ethoxybutyraldehyde, bis-(thiosemicarbazone), or nitrilotriacetic acid. Most preferably, the copper chelate is a chelate of nitrilotriacetic acid.

The SMETH and the copper chelate may be administered either simultaneously, either as a single composition or as independent compositions, or sequentially. Preferably, the SMETH and copper chelate are administered independently. The timing of the administration of the two components should be such that the two components simultaneously achieve effective concentrations in the body so as to form an effective amount of the inhibitory complex between SMETH and the copper of the copper chelate. The dose administered to an animal, particularly a human, in the context of the present invention should be sufficient to effect a therapeutic response in the animal over a reasonable time frame. The dose will be determined by the strength of the particular compound employed and the condition of the animal, as well as the body weight of the animal to be treated. The size of the dose also will be determined by the existence, nature, and extent of any adverse side effects that might accompany the administration of a particular compound.

The SMETH is preferably administered in a concentration of from about 0.001M to about 0.02M. Preferably, the copper chelate is administered in a concentration of up to about 0.02M, without material toxicity. The SMETH and copper chelate may be administered in a pharmaceutically acceptable carrier. Pharmaceutically acceptable carriers are well-known to those who are skilled in the art. The choice of carrier will be determined in part by the particular compound, as well as by the particular method used to administer the composition. It is necessary that the pharmaceutically acceptable carrier lack a reducing agent, such as ascorbic acid, a sulphite, or another similar reducing agent. Accordingly, there is a wide variety of suitable formulations of the pharmaceutical composition of the present invention.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The SMETH and the copper chelate in the context of the present invention, alone or in combination with other suitable components, can be made into aerosol formulations for administration by inhalation. These aerosol formulations can be placed into pressurized acceptable propellants, such as dichlorodifluoromethane, propane, nitrogen, and the like.

Formulations suitable for intravenous and intraperitoneal administration, for example, include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

If the SMETH and the copper chelate are administered in a single pharmaceutical formulation, the formulation should be such that the SMETH and the copper of the copper chelate do not form the inhibitory complex until the site to be treated is contacted.

The method may additionally comprise the administration of an effective amount of one or more glutamine aminotransferase inhibitors. The glutamine aminotransferase inhibitor may be azaserine, diazo-oxonorleucine, or acivicin.

Additionally or alternatively, the method may comprise the administration of an effective amount of one or more amino acids that potentiate the activity of SMETH. Such amino acids include L-leucine, S-ethyl-L-cysteine, DL-isopropionine, L-methionine, and L-norleucine.

If desired, the action of the inhibitory complex, which forms as a result of the administration of SMETH and the copper chelate, may be prevented or reversed. This may be accomplished by the subsequent administration of glutamine or cytidine, for example. In the treatment of some individuals with the pharmaceutical composition of the present invention, it may be desirable to utilize a "mega-dosing" regimen. In such a treatment, a large dose of the pharmaceutical composition is administered to an individual, time is allowed for the active compound, i.e., the inhibitory complex that forms between SMETH and the copper of the copper chelate, to act, and then a suitable reagent, e.g., glutamine or cytidine, is administered to the individual to render the inhibitory complex either less effective or ineffective.

The desirable extent of the inhibition of cell proliferation rate will depend on the particular condition or disease being treated, as well as the stability of the patient and possible side-effects. In proper doses and with suitable administration of certain compounds, the present invention provides for a wide range of the inhibition of the rate of cell proliferation, e.g., from little inhibition to essentially full inhibition.

The present inventive method is expected to be effective in the treatment of all types of cancer. In particular, the present inventive method is expected to have utility in the treatment of ovarian cancer, especially, ovarian cancer that has spread through the peritoneum.

The present invention also provides a pharmaceutical composition for use in the present inventive method. The pharmaceutical composition in accordance with the present invention comprises an effective amount of SMETH (DL or L), an effective amount of a copper chelate, and a pharmaceutically acceptable carrier. The SMETH and the copper of the copper chelate are capable of forming an effective amount of an inhibitory complex that is capable of inhibiting the proliferation of cells contacted by the inhibitory complex. The composition may be administered to a mammal, in particular a human, by any suitable means. The composition is preferably administered by injection or infusion, such as intravenous or intraperitoneal injection or infusion. The composition may be comprised of either a racemic mixture of the D and L stereoisomers of SMETH (DL-SMETH) or the L stereoisomer (L-SMETH) alone. The copper chelate in the composition may be any suitable copper chelate. Preferably, the copper chelate is non-toxic and the copper of the copper chelate is capable of readily forming an inhibitory complex with SMETH. Preferably, the copper chelate is that of nitrilotriacetic acid or any bis(thiosemicarbazone), such as 2-keto-3-ethoxybutyraldehyde, bis-(thiosemicarbazone). Most preferably, the copper chelate is that of nitrilotriacetic acid. Preferably, the SMETH is present in the pharmaceutical composition in a concentration of from about 0.001M to about 0.02M and the copper chelate is present in said pharmaceutical composition in a concentration of up to about 0.02M. The pharmaceutical composition must be free from reducing agents, in particular ascorbic acid, sulphites, and other known reducing agents.

The pharmaceutical composition of the present invention may additionally comprise an effective amount of one or more glutamine aminotransferase inhibitors. The glutamine aminotransferase inhibitor may be azaserine, diazo-oxo-norleucine, or acivicin.

Additionally or alternatively, the composition may comprise an effective amount of one or more amino acids that potentiate the activity of SMETH. The potentiating amino acid may be L-leucine, S-ethyl-L-cysteine, DL-isopropionine, L-methionine, or L-norleucine.

In addition to a method and a composition, the present invention also provides a pharmaceutical kit. The pharmaceutical kit comprises an effective amount of SMETH (DL or L) and an effective amount of a copper chelate, which upon combination form an effective amount of an inhibitory complex that is capable of inhibiting the proliferation of cells contacted by the inhibitory complex. It is preferred that the SMETH and the copper chelate are in pharmaceutically acceptable carriers. Alternatively, the pharmaceutically acceptable carrier may be separate from the SMETH and the copper chelate in the kit. The SMETH and copper chelate may be administered to a mammal, in particular a human, by any one of a number of suitable methods. It is preferred that the SMETH and the copper chelate are administered by injection or infusion, whether intravenous or intraperitoneal. The SMETH may be a racemic mixture of the D and L stereoisomers (DL-SMETH) or the L stereoisomer alone (L-SMETH). The copper chelate may be any suitable copper chelate. It is preferred that the copper chelate be non-toxic and that the copper of the copper chelate be capable of readily forming an inhibitory complex with SMETH. Preferably, the copper chelate is that of nitrilotriacetic acid or any bis-(thiosemicarbazone), such as 2-keto-3-ethoxybutyraldehyde, bis-(thiosemicarbazone). Most preferably, the copper chelate is that of nitrilotriacetic acid.

The following examples serve to further illustrate the present invention but are not intended to limit the scope of the invention.

EXAMPLE 1

This example describes the preparation of S-(methylthio)-DL-homocysteine (DL-SMETH).

S-(methylthio)-DL-homocysteine was prepared from DL-homocysteine (Research Organics, Inc., Cleveland, Ohio) and methyl methanethiosulfonate (Fairfield Chemical Company, Blythewood, S.C.) by a modification of the methylthiolation of L-cysteine as described by Smith et al. (*Biochemistry*, 14, 766–771 (1975)). The L-enantiomorph, L-SMETH, was prepared following reduction of L-homocysteine (Sigma Chemical Company, St. Louis, Mo.) with sodium in liquid ammonia. The excess sodium was removed by the addition of ammonium chloride and the ammonia evaporated at room temperature under nitrogen. The residue was dissolved in oxygen-free water and the solution was neutralized to pH 6.5–7.0 with hydrochloric acid. A 1.25 molar excess of methyl methanethiosulfonate in ethanol was added slowly and the product crystallized after two hours in an ice bath. The crystals were washed with ethanol and peroxide-free ether and dried over phosphorus pentoxide. An analysis was conducted (performed by Atlantic Microlab. Inc., Atlanta, Ga.) for SMETH, which was calculated as C, 33.13; H, 6.12; N, 7.73; and S, 35.37. Similarly, DL-SMETH was calculated as C, 33.21; H, 6.12; N, 7.71; and S, 35.28. L-SMETH was calculated as C, 33.19; H, 6.12; N, 7.68; and S, 35.30. The racemate was resolved into two peaks and the chiral purity of L-SMETH was determined to be at least 99.9% by column chromatography using a resolving column.

EXAMPLE 2

This example describes the inhibition of cell growth using SMETH.

An L1210 established murine leukemia line was maintained in RPMI 1630 medium (Quality Biologicals, Gaithersburg, Md.) containing 16.5% fetal bovine serum (Advanced Biotechnologies, Silver Spring, Md.) and 40 µg/ml gentamycin (Schering Corp., Kenilworth, N.J.). cytotoxicity of SMETH was assessed as follows. Cells were harvested at mid-log phase ($8-10 \times 10^5$ cells/ml), washed with fresh growth medium, and resuspended at $1 \times 10^5$ cells/ml as determined by a model ZBI Coulter Counter (Coulter Electronics, Hialeah, Fla.). Suspensions (7 ml) were added to 25 cm$^2$ Corning flasks to which SMETH, 20 mM in water, either with or without copper sulfate, 2 mM in water, was added as a dilution of water less than or equal to 10 µl/ml of the cell suspension.

Cells were grown at 37° C. for designated times in tightly stoppered flasks. Cell density was determined as indicated above. Cell volume distribution was monitored with a C1000 Channelyzer with standard size latex particles (Coulter) as reference. The results are expressed as growth fraction ($N-N_0/N_0$) or as percent growth fraction compared to appropriate controls.

SMETH was cytotoxic to L1210 cells in culture over a broad range of micromolar concentrations. The range of inhibitory concentrations was both reduced and narrowed in the presence of copper ion (FIG. 1), when the cells were incubated for 40 hours. The copper ion was very effective at micromolar concentrations in bringing a threshold level of SMETH (25 µM) to a completely inhibitory concentration (FIG. 2), while being nontoxic, itself, at much higher levels, when the cells were incubated for 40 hours (see FIG. 3, Mohindru et al., *Biochem. Pharmacol.*, 32, 3627-3632 (1983)). A concentration of 10 µM was more than adequate as a potentiating dose but, at this concentration, other metal ions, such as $Zn^{++}Mn^{++}Co^{++}Ni^{++}Fe^{++}$ and $Cr^{++}$ were ineffective.

Figure 2:
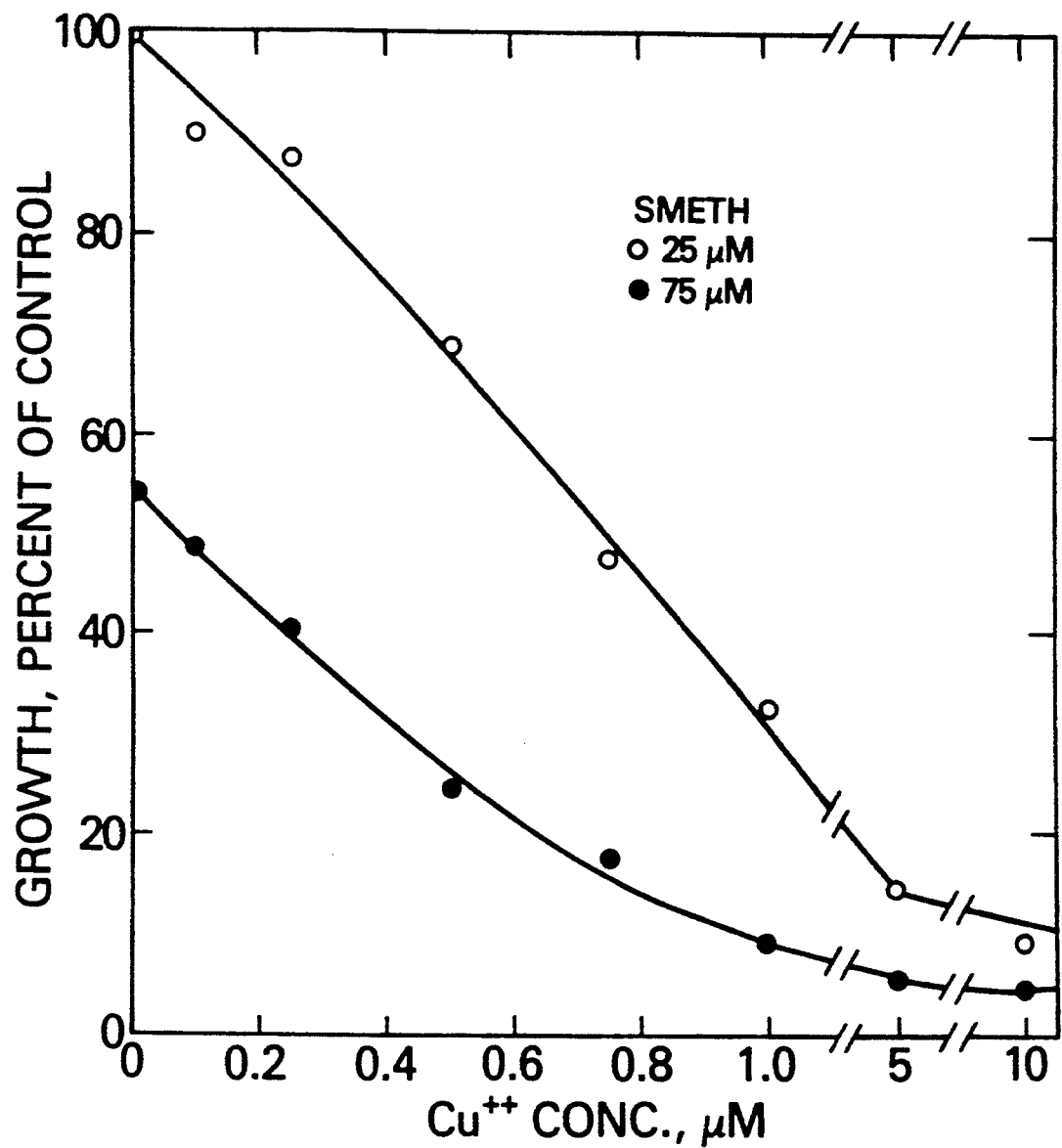
FIG. 2 shows the potentiation of the inhibitory activity of DL-SMETH by copper at threshold and $ID_{50}$ concentrations of SMETH.
Figure 3:
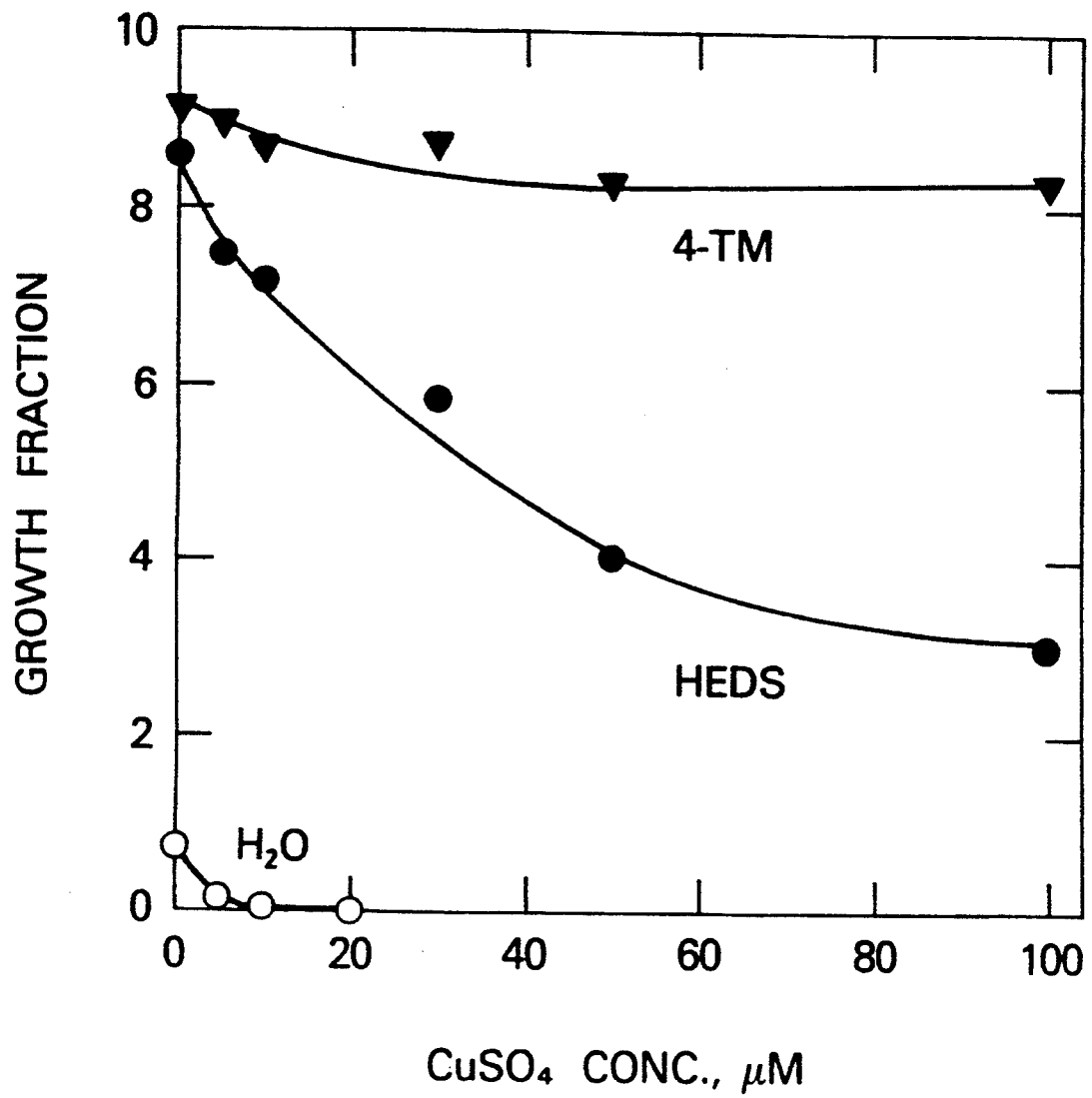
FIG. 3 shows that the lower homolog of SMETH protects L1210 cells in primary culture from copper-induced cytotoxicity.

For the data in FIG. 3, the incubation was performed as in FIG. 2, except that the L1210 cells were obtained directly from the mouse (Mohindru et al.). Such cells fail to grow unless supplemented with an appropriate mercaptan or disulfide (FIG. 3, curve o—o). Hydroxyethyl disulfide (HEDS), the oxidized form of mercaptoethanol, promoted growth, but this was inhibited by high copper concentrations (FIG. 3, curve ●—●). The lower homolog of SMETH namely S-(methylthio)-L-cysteine or 4-thiamethionine (4-TM), is not cytotoxic in the presence of copper and actually protected L1210 cells in primary culture from growth inhibition by copper (FIG. 3) due to depletion of cysteine (Mohindru et al., *Experientia*, 41, 1064-1066 (1985)). At a concentration of 50 µM, 4-TM supported growth that was independent of copper ion concentration (FIG. 3, curve ▼—▼). Thus, both the organic and inorganic moieties of this invention show high specificity in this inhibition.

Figure 4:
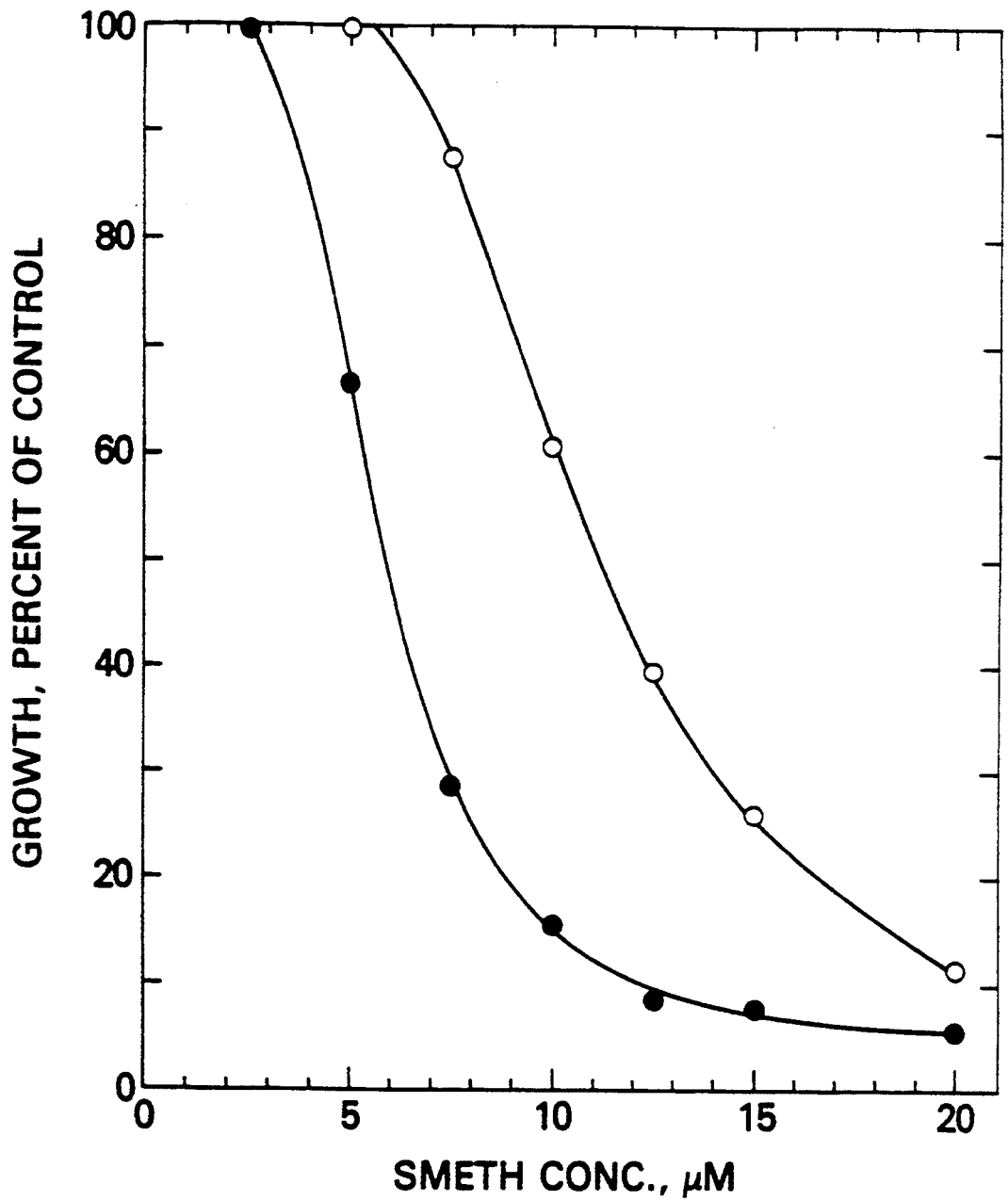
FIG. 4 shows that the cytotoxicity of SMETH is stereospecific.

The racemic form (DL) of SMETH, however, was half as active as L-SMETH (FIG. 4). D-SMETH was completely inactive at 50 µM with 50 µM copper ion. The incubation was performed with copper ion at 50 µM as described in FIG. 1 with S-(methylthio)-DL-homocysteine, DL-SMETH (FIG. 4, curve o—o), and with the pure L-enantiomorph, L-SMETH (FIG. 4, curve ●—●). The use of 10 µM copper sulfate produced nearly identical results.

EXAMPLE 3

This example describes the determination of the site of inhibition.

Figure 5:
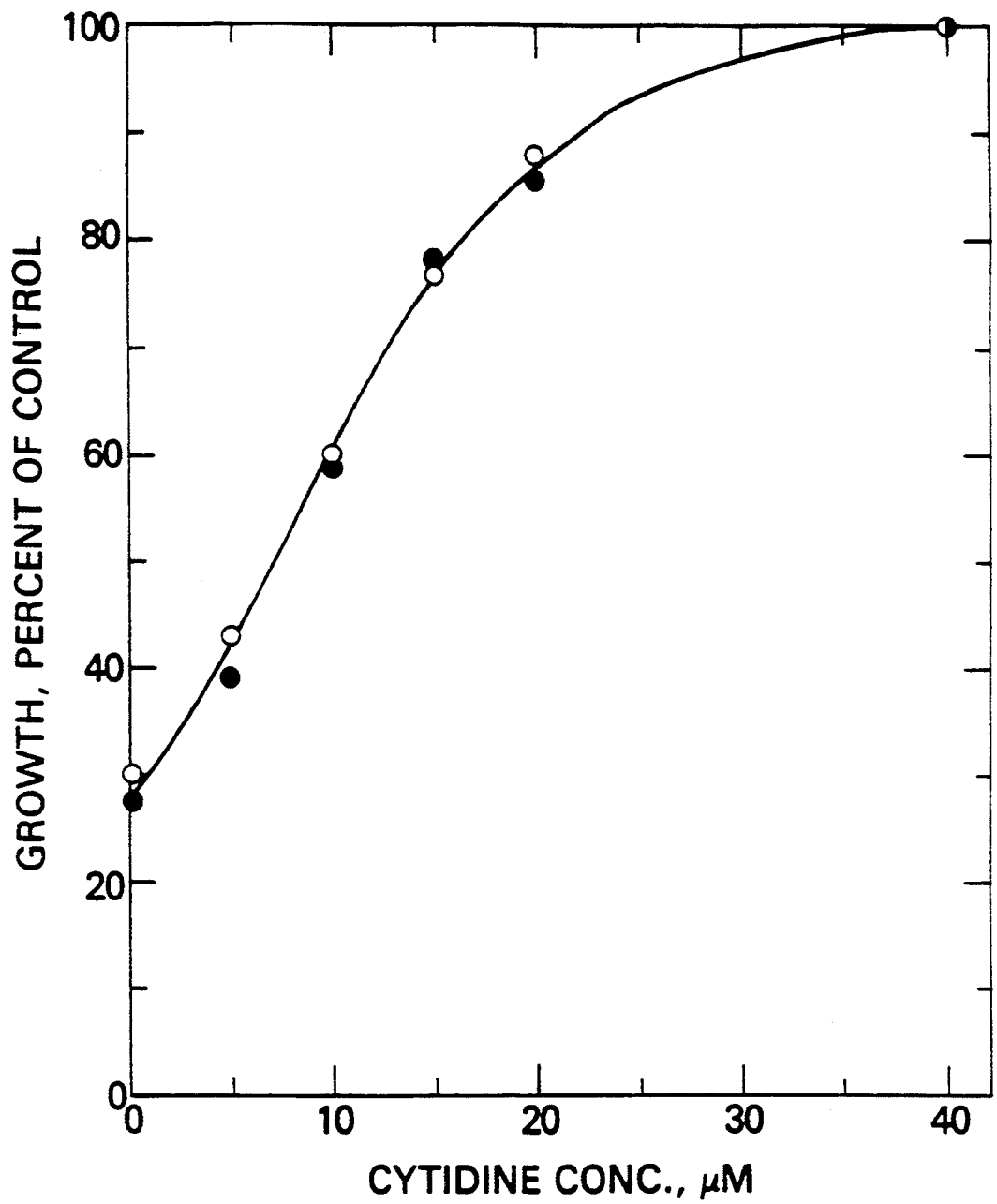
FIG. 5 shows that cytidine protects L1210 cells from the cytotoxicity of S-(methylthio)-L-homocysteine (L-SMETH) and copper ion.

The amination of uridine-5'-triphosphate (UTP) to cytidine-5'-triphosphate (CTP), which is one of the several biochemical roles of glutamine, is the only locus blocked by SMETH plus copper. Two observations led to this conclusion. One observation is that cytidine, alone, protected the cells from growth inhibition in a noncompetitive manner, i.e., equivalent concentrations of cytidine were equally effective at two concentrations of SMETH plus copper that maximally inhibited cell growth (FIG. 5). The other observation is that HPLC analysis of growth-inhibited cells showed greater than a ⅔ diminution of CTP content but a twofold elevation of UTP, ATP and GTP (FIG. 6).

The data in FIG. 5 were obtained by incubating the cells with 15 µM (curve o—o) and 30 µM (curve ●—●) L-SMETH, together with corresponding concentrations of copper sulfate. Uridine and guanosine were ineffective in such protection.

Figure 6B:
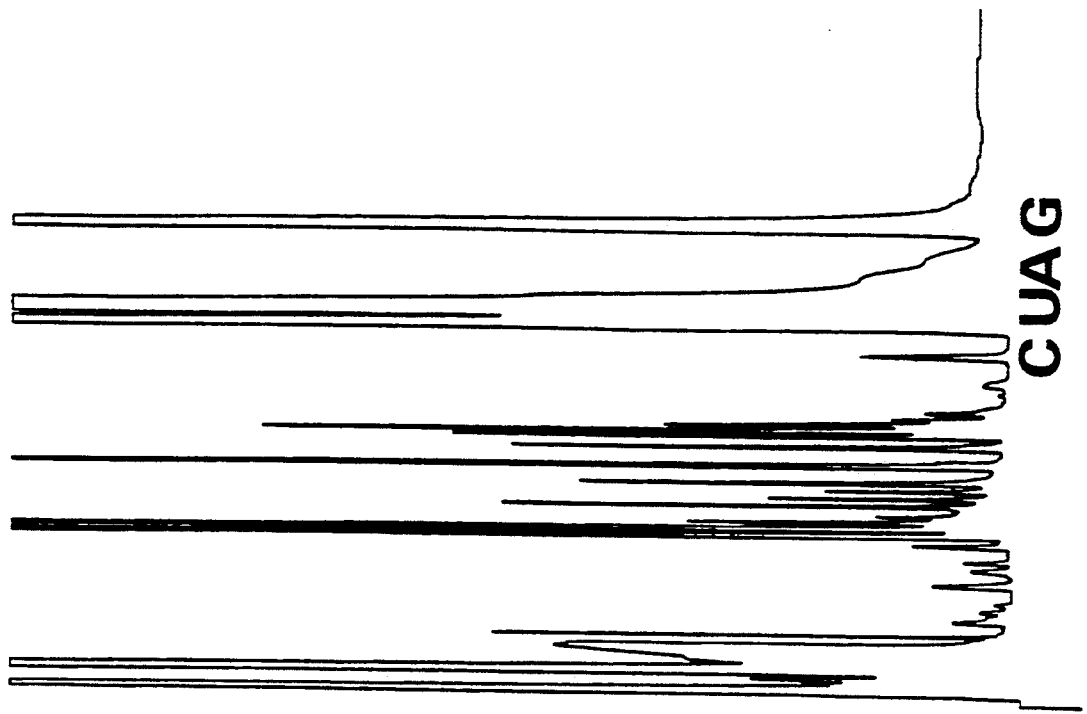
FIG. 6 presents the analysis of the nucleoside triphosphate content of cells incubated without and with L-SMETH and copper ion.
Figure 6A:
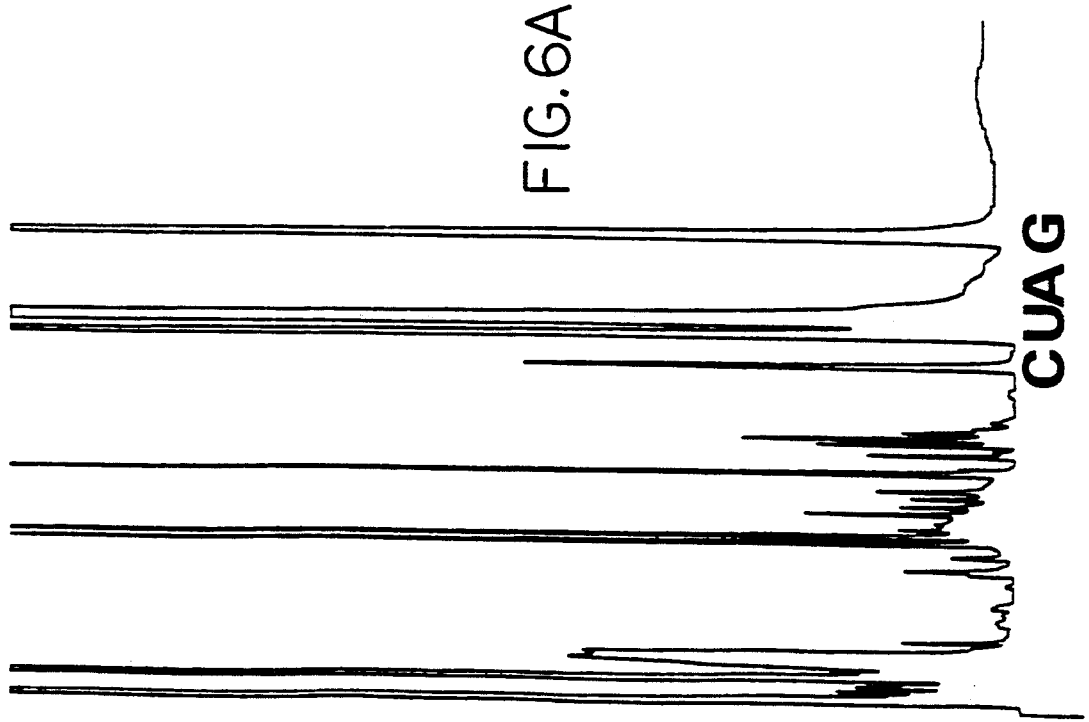

The data in FIG. 6 were obtained by incubating the cells in the medium described in Example 2 but which contained only half of the normal concentration of glutamine, i.e., 1 mM. The inhibited culture also contained 15 µM each of L-SMETH and copper sulfate.

At the end of the incubation, the cell density in the inhibited culture was determined, and the entire population was centrifuged for analysis. An aliquot containing an equal number of cells from the control culture was removed for comparison. Both samples were processed and the nucleoside triphosphate pools were analyzed. The total incubation volume of the samples was increased to 100 ml in 175 cm$^2$ flasks, although the same proportions of cells and solutions were used. At the appropriate time, growth was terminated by shaking the flasks in ice. All further steps were performed with ice-cold reagents under refrigerated conditions. On reaching 4° C., the cells were pelleted in a refrigerated centrifuge and extracted with 500 µl of 10% TCA. The precipitate was sedimented in a microcentrifuge tube and the supernatant fluid was transferred to another tube and extracted vigorously with an equal volume of 4:1 freon: tri-n-octylamine by volume as described by Khym (*Clin. Chem.*, 21, 1245-1252 (1975)). The supernatant fluid was removed and 200 µl was analyzed by HPLC with the use of a Whatman 5SAX column (12.5×0.4 cm) and ammonium phosphate, pH 3.5, gradient (0.02 m to 0.7 m) over 40 minutes. The detection of components was made by UV absorbance at 254 nm.

The left panel of FIG. 6 represents control samples, whereas the right panel of FIG. 6 represents inhibited culture samples. The separated nucleotide triphosphates with their retention times (RT) and the effect of SMETH plus copper relative to the control sample are as follows:

cytidine triphosphate (C): RT=20.0 min. 29% decrease uridine triphosphate (U): RT=21.3 min. 233% increase adenosine triphosphate (A): RT=22.6 min. 196% increase guanosine triphosphate (G): RT=27.5 min. 186% increase The modal volume of the control cells was 820 µ$^3$, whereas that of the inhibited cells was 1140 µ$^3$. Other uncharacterized peaks were also elevated in the inhibited sample. Such elevated levels of cellular constituents may be due to the increased volume of inhibited cells.

EXAMPLE 4

This example describes the cell expansion and unbalanced growth that accompanies growth inhibition by SMETH and SMETH plus copper.

Figure 7:
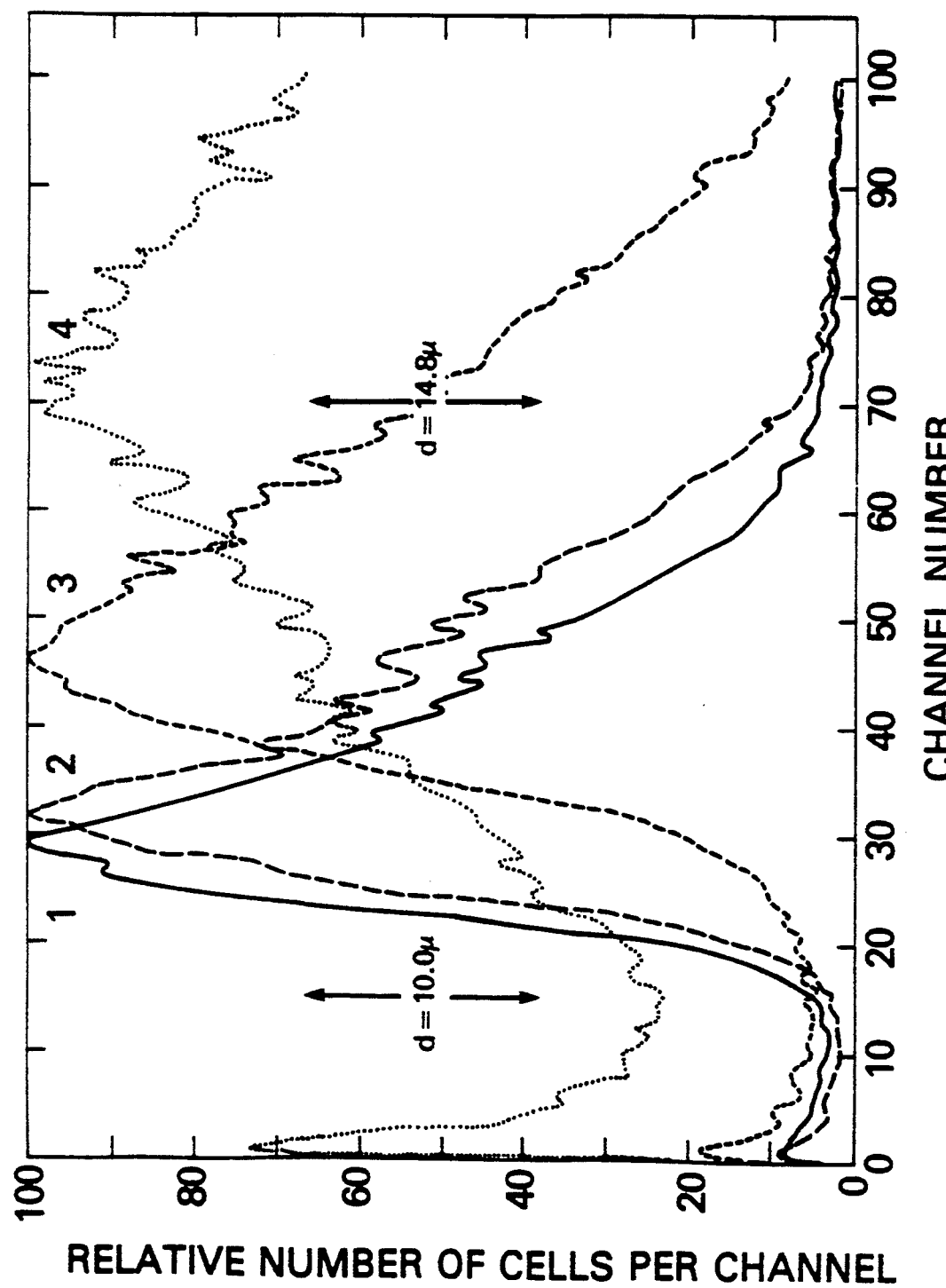
FIG. 7 shows the progression of the increase in volume and the lysis of L1210 cells from inhibited cultures.

SMETH and SMETH plus copper induced growth inhibition is characterized by a progressive increase in cell volume that is observed over a two-day period (FIG. 7). The data in FIG. 7 were obtained by incubating cells under standard conditions with 15 μM L-SMETH and 15 μM copper sulfate. Cell volume was monitored during the course of the incubation. Curve 1 denotes control cells, which have a modal volume of 870 $\mu^3$. Curve 2 denotes inhibited cells, which were inhibited for 16 hours and which have a modal volume of 915 $\mu^3$. Cells inhibited for 24 hours with a modal volume of 1270 $\mu^3$ are represented by curve 3, whereas cells inhibited for 40 hours with a modal volume of 1820 $\mu^3$ are represented by curve 4. Ultimately, the cells burst as indicated by the accumulation of debris shown near the ordinate.

Flow cytometric analysis of control and inhibited, swollen cells was carried out as follows. Cells were incubated for 24 hours without and with L-SMETH and copper sulfate as described with regard to FIG. 6. After incubation, cell number and cell volume distribution (FIG. 8, lower panel) were determined and an equal number of cells were removed, fixed and stained with fluorescein isothiocyanate and propidium iodide as described by Crissman et al. (*Cytometry*, Z, 59–62 (1981)). Samples were analyzed on a Becton Dickinson FACS 440 flow cytometer (Becton Dickinson, Mountain View, Calif.). The argon ion laser (Coherent Innova 90-5, Palo Alto, Calif.) was tuned to 488 nm and operated at a power output of 200 mw in the light-stabilized mode. Fluorescein isothiocyanate fluorescence and propidium iodide fluorescence were determined with the use of a 535/15 and a 630/22 band pass filter, respectively. Data from over $1 \times 10^4$ cells were collected from each sample and analyzed in a Becton Dickinson Consort 40 computer system.

Figure 8:
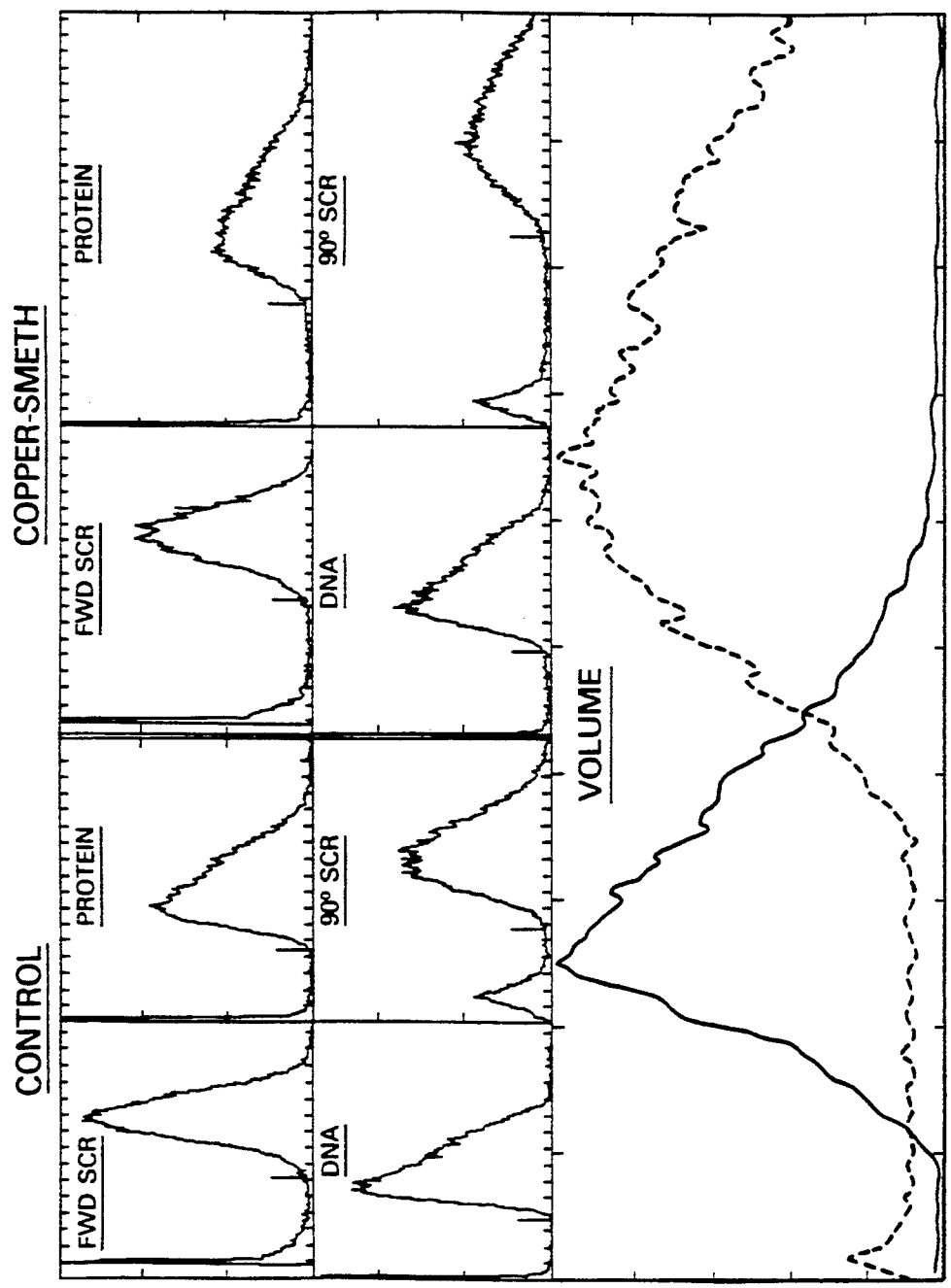
FIG. 8 illustrates the flow cytometric analysis of L1210 cells from cultures inhibited with L-SMETH and copper ion. FWD SCR=forward scatter. 90° SCR=90° scatter of light. The abscissa denotes the magnitude of the substance shown in the panel. The ordinate denotes the relative number of cells.

Flow cytometric analysis of control and inhibited, swollen cells showed an increase in fluorescein isothiocyanate staining and propidium iodide staining in the inhibited cells relative to the control cells, which is indicative of increases in protein and DNA per cell, respectively (FIG. 8). Inhibited cells showed a 60% increase in protein, a 35% increase in DNA, and a 100% increase in volume. The correspondence between protein distribution and 90° scatter with volume distribution of the cells is particularly striking.

The marked swelling and lysis from the SMETH and SMETH plus copper promoted CTP deficiency may be a consequence of a block in phospholipid biosynthesis for plasma membrane generation (Vance, in: *Biochemistry of Lipids and Membranes*, Vance and Vance, eds., pages 242–270 (1985)). Both DNA and protein synthesis continue in the inhibited swollen cells. Also, the Km of the reactions involving CTP in phospholipid biosynthesis is higher than those of nucleic acid formation (Vance). Thus, as the availability of CTP becomes limiting, a block in phospholipid biosynthesis would be the first to become evident and could result in unbalanced growth, membrane pathology, swelling and lysis.

EXAMPLE 5

This example demonstrates that the toxicity of SMETH is not due to the delivery of homocysteine.

SMETH was originally synthesized as a prodrug to deliver homocysteine to cells, being modeled after the lower homolog S-(methylthio)-cysteine (Rabinovitz et al., *Biochem. Pharmacol.*, 7, 100–108 (1961)), which upon intracellular reduction of the disulfide bond, delivers cysteine to cells (Mohindru et al., *Proc. Am. Assoc. Cancer Res.*, 24, 1 (1983); Pierson et al., *Cancer Res.*, 45, 4727–4731 (1985)). Similar delivery of homocysteine was expected to promote the formation of S-adenosylhomocysteine, which is a potent inhibitor of cellular methylations (Ueland, *Pharmacol. Rev.*, 34, 223–253 (1982)) and a projected end product for chemotherapy Borchart, *J. Med. Chem.*, 23, 347–357 (1981). Inhibition analysis, however, indicated that cytotoxicity was not due to homocysteine delivery.

Such toxicity has been reported for homocysteine thiolactone, which in combination with added adenosine and an adenosine deaminase inhibitor, such as deoxycoformycin, can block growth due to adenosylhomocysteine formation Kredich et al. PNAS, 76, 2450–2454 (1979)). Adenosylhomocysteine is a potent inhibitor of cellular methylation processes and, as an endogenous product of methionine metabolism trapped intracellularly by added adenosine, is the reported basis for adenosine toxicity (Kredich et al., *Cell*, 12, 931–938 (1977)).

The toxicity of adenosine was evaluated over a concentration range of 5 to 40 μM. At 10 μM, it was not toxic to L1210 cells, but, when added together with a non-toxic concentration of L-homocysteine thiolactone, it was toxic. However, adenosine did not increase the potency of a toxic dose of SMETH (Table I). The failure of adenosine to promote SMETH toxicity suggests that such toxicity is not due to adenosylhomocysteine formation.

TABLE I

|  | % Inhibition* |
|---|---|
| 200 μM-Homocysteine Thiolactone | 5 |
| plus 10 μM Adenosine | 39 |
| 75 μM DL-SMETH | 46 |
| plus |  |
| 10 μM Adenosine |  |
| 20 μM deoxycoformycin | 46 |

*Percent inhibition is determined from the percent growth fraction obtained with and without the compounds indicated.

EXAMPLE 6

This example demonstrates the protection of cells by glutamine from growth inhibition by SMETH and SMETH plus copper.

Millimolar concentrations of glutamine supported cell growth and protected cells against growth inhibition by SMETH and SMETH plus copper (Table II). Glutamine protected cells in a competitive manner. In the given range of concentrations of glutamine, the full range from complete inhibition to complete protection is evident.

TABLE II

| Glutamine Concentration (mM) | Growth as Percent of Control (50 μM L-SMETH) | Growth as Percent of Control (10 μM L-SMETH, 10 μM $Cu^{++}$) |
|---|---|---|
| 0.5 | 15 | 0 |
| 1.0 | 31 | 7.7 |
| 2.0 | 58 | 58 |
| 4.0 | 98 | 100 |

EXAMPLE 7

This example demonstrates the potentiation of growth inhibition by SMETH with amino acids other than glutamine.

The type of protection observed for glutamine was not observed for other amino acids, such as L-leucine, S-ethyl-L-cysteine, DL-isopropionine, L-methionine, and L-norleucine, some of which resemble SMETH more closely in structure. These amino acids actually promoted SMETH toxicity (Table III).

TABLE III

| Potentiating Amino Acid | mM* Amino Acid to Increase Inhibition of DL-SMETH by 50% |
|---|---|
| L-leucine | 1 |
| S-ethyl-L-cysteine | 1 |
| DL-isopropionine | 2 |
| L-methionine | 2 |
| L-norleucine | 2.5 |

*Estimated by interpolation. The DL-SMETH concentration was 75 or 100 μM.

The promotion of inhibitory activity may be due to the phenomenon referred to as "trans-stimulation of uptake", which is common in the amino acid series (Schafer et al., Biochem. Biophys. Acta, 135, 741–750 (1967)). Such increased uptake would increase cytotoxicity.

It should be noted that SMETH has the same amino to disulfide configuration as does homocystine, and that the cuprous ion has nearly identical reactivities as a silver ion (Cotton et al., Advanced Inorganic Chemistry, 4th edition, John Wiley & Sons, NY, page 966 (1980)). Cecil et al. (Biochem. J., 66, 538–543 (1957)) observed that homocystine reacted with silver ion at a rate that is 267 times that of cystine and that this increased rate was dependent upon the presence of unsubstituted amino groups. They (Cecil et al., Adv. Protein Chem., 14, 299–302 (1959)) indicated that the metal ion was bound by amine formation and, therefore, that it was brought closer to the disulfide bond. Appropriate configuration required that two methylene groups were spaced between the unsubstituted amino group and the disulfide, possibly to allow hydrogen bond formation in the unsubstituted amino acid. Accordingly, a similar reaction rate did not occur with cystine.

The coordination between the cuprous ion and a symmetrical disulfide (Ottersen et al., Inorg. Chem., 13, 1904–1911 (1974)) involves a lengthening of the disulfide bond and thus its weakening. In essence:

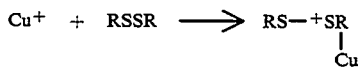

The

moiety thus becomes a much better leaving group than the original —SR. The sulfur-sulfur bond becomes more susceptible to nucleophilic attack and the structure may be considered an example of an intermediate in concomitant electrophilic and nucleophilic catalysis of the scission of this bond (Kice, Accts. Chem. Res., 1, 58–64. (1968); Kice. The Sulfur-Sulfur Bond, in: *Sulfur in Organic and Inorganic Chemistry*, Vol. 1. A. Senning, ed. Marcel Dekker, N.Y. pages 195, 196 (1971)). The reaction would be as follows:

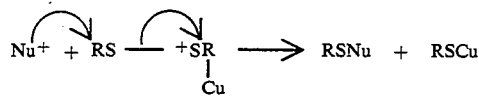

Figure 9A:
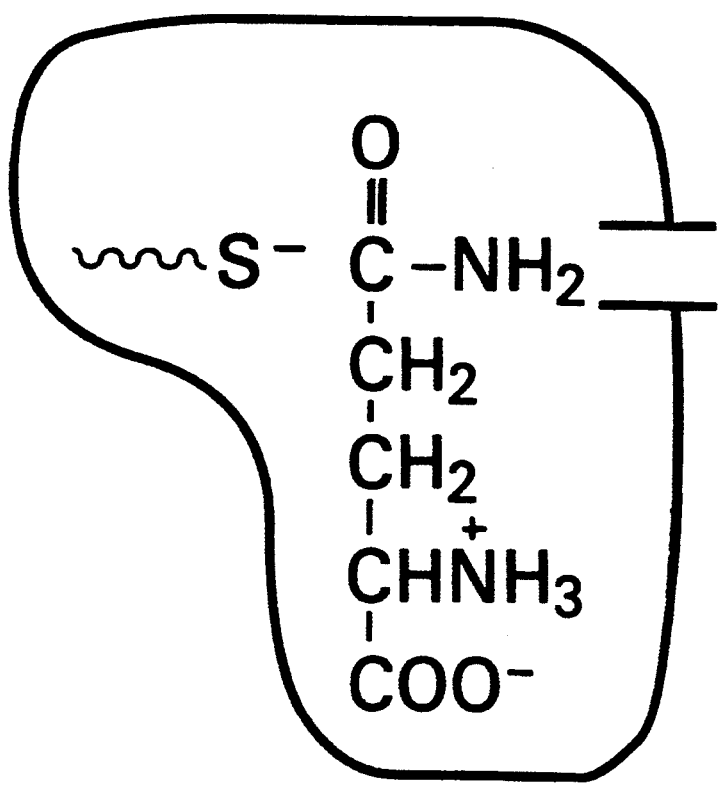
FIG. 9 provides diagrammatic representations of the inhibitory complex of SMETH and copper (right panel) at the reactive site of the enzyme and of glutamine (left panel) at the reactive site of the enzyme.
Figure 9B:
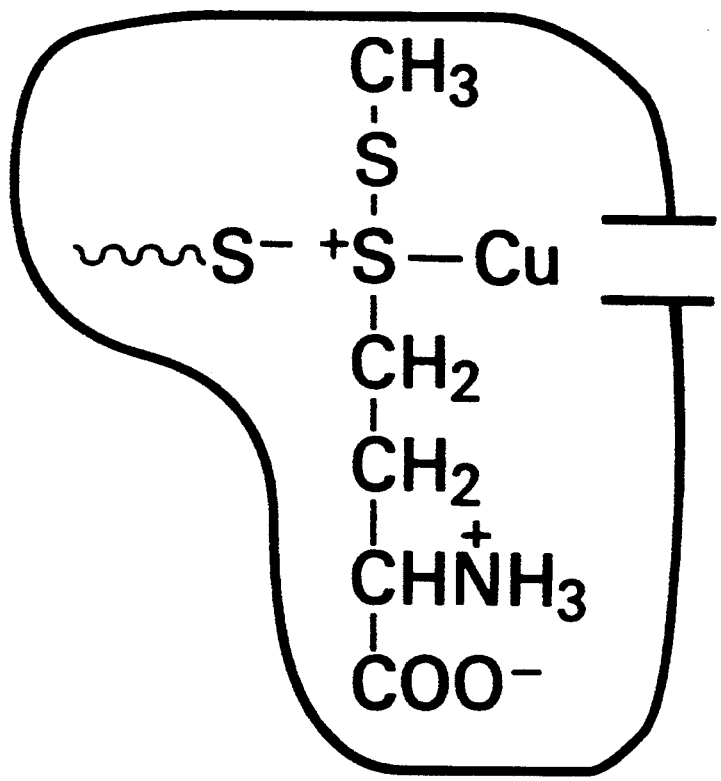

In accordance with such a reaction, the cuprous sulfide of homocysteine would act as the leaving group and the enzyme would be methylthiolated if L-SMETH plus copper were to occupy the active site of the enzyme CTP synthetase (FIG. 9, right panel). This is based on the positioning of glutamine in CTP synthetase relative to its reactive thiolate anion (Levitzki et al., The Allosteric Control of CTP Synthetase, in: *The Enzymes of Glutamine Metabolism*, Pruisner et al., eds. Academic Press, N.Y., pages 505–521 (1973)) as shown in FIG. 9, left panel. In the reaction of glutamine and CTP synthetase, the glutamine loses its amide group and reacts to form a thio-ester. The positioning of L-SMETH plus copper is dependent upon the "natural" L configuration of SMETH and places the nucleophilic thiolate ion in close proximity to the sulfonium moiety of the copper disulfide function. However, the possibility that migration of the copper to the sulfur of the methylthio moiety of SMETH would make the methylthio moiety the leaving group cannot be ignored.

The activity of SMETH plus copper differs from that of the natural aminotransferase inhibitors azaserine, diazo-oxo-norleucine and acivicin in that only one critical cellular pathway is blocked—the amination of UTP to CTP. The other inhibitors also block some sites in purine biosynthesis (Livingston et al., Adv. Pharmacol. Chemotherap., 8, 57–120 (1970)) including the amination step for the synthesis of guanosine monophosphate (Neil et al., Adv. Enzyme Regul., 17, 375–398 (1978); Neil et al., Cancer Res., 39, 852–865 (1979)). Currently, there is no explanation for this difference. However, it should be noted that the reactive center of SMETH plus copper is internal (FIG. 9), whereas the reactive site may be considered to be terminal in the other glutamine analogs. Accordingly, bulk tolerance should be taken into consideration so that the methylthio and copper moieties, for example, are acceptable within the active site of the enzyme.

Homocysteine has been shown to promote endothelial cell damage via copper-catalyzed hydrogen peroxide generation (Starkebaum et al., J. Clin. Invest., 77, 1370–1376 (1986)). The adenosyl derivative of homocysteine has been shown to be toxic by blocking methionine metabolism (Djurhuus et al., Carcinogenesis, 9, 9–16 (1988)). Homocysteine thiolactone may be toxic due to acylations of cellular constituents by the reactive thiolactone moiety (Dudman et al., Biochem. Med., 27, 244–253 (1982)). These alternative mechanisms of cytotoxicity may be considered to be inoperative in the present system since cells can be protected from SMETH and SMETH plus copper inhibition by glutamine and cytidine.

All of the references identified herein are hereby incorporated by reference in their entireties.

While this invention has been described with an emphasis upon preferred embodiments, it will be obvious to those of ordinary skill in the art that variations in the preferred methods, compounds, compositions, and kits can be used and that it is intended that the invention can be practiced otherwise than as specifically described herein. Accordingly, this invention includes all modifications encompassed within the spirit and scope of the invention as defined by the appended claims.

What is claimed is:

1. A method of inhibiting in a mammal proliferation of non-quiescent cells susceptible to treatment with an effective amount of S-(methylthio)-homocysteine and a copper chelate, which method comprises administering to said mammal an effective amount of S-(methylthio)-homocysteine selected from the group consisting of the L stereoisomer and a racemic mixture of the D and L stereoisomers of S-(methylthio)-homocysteine and an effective amount of a copper chelate, the copper of which readily forms an inhibitory complex with S-(mehylthio)-homocysteine, such that an effective amount of the inhibitory complex forms in the mammal between said S-(methylthio)-homocysteine and the copper of said copper chelate so as to inhibit the proliferation of non-quiescent cells contacted by said effective amount of said inhibitory complex.

2. The method of claim 1, wherein said mammal is a human.

3. The method of claim 1, wherein said administration is by a method selected from the group consisting of intravenous injection, intraperitoneal injection, intravenous infusion, and intraperitoneal infusion.

4. The method of claim 1, wherein said S-(methylthio)-homocysteine is a racemic mixture of the D and L stereoisomers of S-(methylthio)-homocysteine.

5. The method of claim 1, wherein said S-(methylthio)-homocysteine is the L stereoisomer of S-(methylthio)-homocysteine.

6. The method of claim 1, wherein said copper chelate is selected from the group consisting of the copper chelate of nitrilotriacetic acid and the copper chelate of any bis-(thiosemicarbazone).

7. The method of claim 6, wherein said bis(thiosemicarbazone) is 2-keto-3-ethoxybutyraldehyde, bis(-thiosemicarbazone).

8. The method of claim 1, wherein said S-(methylthio)-homocysteine and said copper chelate are administered simultaneously.

9. The method of claim 1, wherein said S-(methylthio)-homocysteine and said copper chelate are administered sequentially.

10. The method of claim 1, wherein said S-(methylthio)-homocysteine is administered in a concentration of from about 0.001M to about 0.02M.

11. The method of claim 10, wherein said copper chelate is administered in a concentration of up to about 0.02M.

12. The method of claim 1, wherein said S-(methylthio)-homocysteine and copper chelate are administered in a pharmaceutically acceptable carrier.

13. The method of claim 12, wherein said pharmaceutically acceptable carrier lacks a reducing agent.

14. The method of claim 1, wherein said non-quiescent cells are cancer cells.

15. The method of claim 14, wherein said cancer cells are selected from the group consisting of carcinoma cells, sarcoma cells, and leukemia cells.

16. The method of claim 14, wherein said cancer cells are leukemia cells.

17. The method of claim 16, wherein said leukemia cells are myeloid leukemia cells.

18. The method of claim 1, wherein said effective amount of S-(methylthio)-homocysteine is from about 0.001M to about 0.02M and said effective amount of a copper chelate is an amount up to about 0.02M.

19. A pharmaceutical composition comprising an effective amount of S-(methylthio)-homocysteine selected from the group consisting of the L stereoisomer, and a racemic mixture of the D and L stereoisomers of c-(methylthio)-homocysteine, an effective amount of a copper chelate, the copper of which readily forms an inhibitory complex with S-(methylthio)-homocysteine and a pharmaceutically acceptable carrier.

20. The composition of claim 19, wherein said composition is suitable for intravenous or intraperitoneal administration to a mammal.

21. The composition of claim 19, wherein said S-(methylthio)-homocysteine is a racemic mixture of the D and L stereoisomers of S-(methylthio)-homocysteine.

22. The composition of claim 19, wherein said S-(methylthio)-homocysteine is the L stereoisomer of S-(methylthio)-homocysteine.

23. The composition of claim 19, wherein said copper chelate is selected from the group consisting of the copper chelate of nitrilotriacetic acid and the copper chelate of any bis-(thiosemicarbazone).

24. The composition of claim 23, wherein said bis(thiosemicarbazone) is 2-keto-3-ethoxybutyraldehyde, bis(-thiosemicarbazone).

25. The composition of claim 19, wherein said S-(methylthio)-homocysteine is present in said pharmaceutical composition in a concentration of from about 0.001M to about 0.02M.

26. The composition of claim 25, wherein said copper chelate is present in said pharmaceutical composition in a concentration of up to about 0.02M.

27. The composition of claim 19, wherein said pharmaceutically acceptable carrier lacks a reducing agent.

28. The composition of claim 19, wherein said effective amount of S-(methylthio)-homocysteine is from about 0,001M to about 0.02M and said effective amount of a copper chelate is an amount up to about 0.02M.

* * * * *